US009304191B2

United States Patent
Nagae et al.

(10) Patent No.: US 9,304,191 B2
(45) Date of Patent: Apr. 5, 2016

(54) SUBJECT INFORMATION OBTAINING APPARATUS, SUBJECT INFORMATION OBTAINING METHOD, AND PROGRAM

(75) Inventors: Kenichi Nagae, Yokohama (JP); Hirofumi Taki, Kyoto (JP); Takuya Sakamoto, Kyoto (JP); Toru Sato, Kyoto (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 14/342,303

(22) PCT Filed: Aug. 29, 2012

(86) PCT No.: PCT/JP2012/072519
§ 371 (c)(1),
(2), (4) Date: Feb. 28, 2014

(87) PCT Pub. No.: WO2013/032018
PCT Pub. Date: Mar. 7, 2013

(65) Prior Publication Data
US 2014/0219060 A1 Aug. 7, 2014

(30) Foreign Application Priority Data

Sep. 2, 2011 (JP) .................................. 2011-191416

(51) Int. Cl.
*G01S 15/00* (2006.01)
*A61B 8/00* (2006.01)
(Continued)

(52) U.S. Cl.
CPC ............... *G01S 7/52* (2013.01); *G01S 7/52028* (2013.01); *G01S 7/52047* (2013.01);
(Continued)

(58) Field of Classification Search
CPC ............ G01S 7/52047; G01S 7/52077; G01S 15/5207; G01S 15/02; G01S 15/8977; A61B 8/5207; A61B 8/0891
See application file for complete search history.

(56) References Cited

U.S. PATENT DOCUMENTS

2003/0018253 A1* 1/2003 Napolitano et al. .......... 600/437
2004/0087857 A1* 5/2004 Napolitano et al. .......... 600/443
(Continued)

FOREIGN PATENT DOCUMENTS

JP 2010-183979 A 8/2010

OTHER PUBLICATIONS

Taki, et al., "High Range Resolution Unitrasonographic Vascular Imaging Using Frequency Domain Interferometry With the Capon Method", IEEE Transactions on Medical Imaging, Feb. 2012, pp. 417-429, Vo. 31, No. 2.
(Continued)

*Primary Examiner* — Luke Ratcliffe
*Assistant Examiner* — Hovhannes Baghdasaryan
(74) *Attorney, Agent, or Firm* — Canon USA Inc. IP Division

(57) ABSTRACT

A subject information obtaining apparatus according includes: plurality of conversion elements configured to convert an elastic wave from a subject into a plurality of reception signals, a delay and sum unit configured to perform a delay and sum process by using the plurality of reception signals and output a plurality of scanning line signals, a scanning line synthesis unit configured to add the plurality of scanning line signals between adjacent scanning lines and output a plurality of synthesis scanning line signals, and an FDI adaptive processing unit configured to perform a frequency domain interferometry and an adaptive signal processing by using the plurality of synthesis scanning line signals and obtain a power intensity distribution.

7 Claims, 11 Drawing Sheets

(51) Int. Cl.
*G01S 7/52* (2006.01)
*G01S 15/89* (2006.01)
*G01S 15/02* (2006.01)
*A61B 8/08* (2006.01)

(52) U.S. Cl.
CPC ............ *G01S 7/52077* (2013.01); *G01S 15/02* (2013.01); *G01S 15/8977* (2013.01); *A61B 8/0891* (2013.01); *A61B 8/5207* (2013.01)

(56) References Cited

U.S. PATENT DOCUMENTS

2005/0043622 A1* 2/2005 Jensen .......................... 600/449
2009/0112093 A1* 4/2009 Bae et al. ...................... 600/447
2009/0299186 A1* 12/2009 Waters et al. ................. 600/449

OTHER PUBLICATIONS

Taki, et al., "High Range Resolution Medical Acoustic Vascular Imaging with Frequency Domain Interferometry", 32 Annual International Conference of the IEEE EMBS Buenos Aires, Argentina, Aug. 31-Sep. 4, 2010, pp. 5298-5301.

Taki, et al., "High Resolution Medical Acoustic Vascular Imaging Using Frequency Domain Interferometry", Proceedings of the Ninth IASTED International Conference Visualization, Imaging, and Image Processing, (VIIP2009) Jul. 13-15, 2009 Cambridge UK pp. 7-13.

* cited by examiner

SUBJECT INFORMATION OBTAINING APPARATUS, SUBJECT INFORMATION OBTAINING METHOD, AND PROGRAM

CROSS REFERENCE TO RELATED APPLICATIONS

This application is a U.S. National Stage of International application No. PCT/JP2012/072519 filed on Aug. 29, 2012 which claims priority from Japanese Patent Application JP 2011-191416 filed Sep. 2, 2011, the disclosures of which are hereby incorporated by reference herein in their entirety.

TECHNICAL FIELD

The present invention relates to a subject information obtaining apparatus, a subject information obtaining method, and a program. In particular, the invention relates to a technology of transmitting an elastic wave to a subject and receiving a reflection wave reflected in the subject to obtain subject information.

BACKGROUND ART

In an ultrasonic diagnosis apparatus functioning as a subject information obtaining apparatus, a spatial resolution in a depth direction in a case where image data is formed through a pulse echo technique can be generally represented by $(n\lambda)/2$ when a wavelength of an ultrasonic wave is set as $\lambda$ and a transmission wave number is set as n. For example, the spatial resolution in the depth direction is approximately 0.13 mm in a case where an ultrasonic wave having a center frequency at 12 MHz is transmitted for two wavelengths.

A description will be provided of the pulse echo technique. First, when an ultrasonic pulse (elastic wave) is transmitted to a subject, an ultrasonic wave is reflected and returned in accordance with an acoustic impedance difference within the subject. Next, this reflection wave is received, and image data is generated by using a reception signal of the reflection wave. Typically, an envelope of the reception signal is obtained, and this envelope is converted into a luminance value to generate the image data. By repeating the transmission and reception of the ultrasonic wave in plural directions or positions within the subject, it is possible to obtain luminance information on plural scanning lines in the directions in which the ultrasonic wave is transmitted and received. Imaging within the subject is enabled by disposing the luminance information on the plural scanning lines.

It is noted that in the ultrasonic diagnosis apparatus, plural conversion elements configured to convert the ultrasonic wave into an electric signal are generally used, and a temporal shift is added to reception signal waveforms between the respective elements to be focused within the subject in both the transmission and the reception.

As described above, the spatial resolution on the order of approximately 0.13 mm in the depth direction can be realized by using the pulse echo technique, but a higher spatial resolution is demanded. For example, if a layered structure of a blood vessel wall of the carotid artery can be observed in further detail, the observation may contribute to an early detection of hardened arteries and the like.

As a technology for improving the above-described spatial resolution in the depth direction, NPL 1 illustrates a result obtained by imaging a layered structure of a blood vessel wall by applying a frequency domain interferometry (FDI) and a Capon technique corresponding to an adaptive signal processing. By applying the FDI and the Capon technique to the reception waveform, it is possible to further improve the spatial resolution in the depth direction (scanning line direction). It is however noted that within a range of the signals in the depth direction cut off for carrying out the FDI processing (within a processing range), plural reflection layers are supposed to exist. Also, plural reflection layers from adjacent reflection layers are likely to mutually have a high correlativity. If the adaptive signal processing such as the Capon technique is directly applied to the reception signals of the plural reflection waves having the above-described high correlativity, an unexpected operation such as a cancellation of a wanted signal occurs. To reduce (suppress) the influence from the signals having the above-described correlativity (correlative interference wave), by using a frequency averaging technique in combination, it is possible to apply the FDI and the Capon technique to the reception signals of the reflection waves.

CITATION LIST

Non Patent Literature

NPL 1 Hirofumi Taki, Kousuke Taki, Takuya Sakamoto, Makoto Yamakawa, Tsuyoshi Shiina and Toru Sato: Conf Proc IEEE Eng Med Biol Soc. 2010; 1:5298-5301.

SUMMARY OF INVENTION

However, in a case where the FDI and the adaptive signal processing are applied to the reception signals of the reflection waves as in NPL 1, since the processing is carried out every scanning line, the degrees of the suppression on the correlative interference wave are not matched in the mutual adjacent scanning lines. As a result, it is found out that a part where a continuity in a direction intersecting with the scanning line is scarce may be generated in the obtained image data.

On the other hand, a spatial resolution in the direction intersecting with the scanning line varies depending on a convergence condition at the time of the transmission and reception of the elastic wave. To realize the imaging without omission of a minute reflector or the like existing in an observation area within the subject, according to the general pulse echo technique, a distance between the scanning lines (scanning line interval) is set to be shorter than a spatial resolution in the direction intersecting with the scanning line. For that reason, in a case where the FDI and the adaptive signal processing are not used, it is conceivable that the continuity between the adjacent scanning lines is not scarce.

To elaborate, by using the FDI and the adaptive signal processing, the continuity in the direction intersecting with the scanning line may be lower than the general image (image obtained by obtaining the envelope of the reception signal), and as a result, a particular problem occurs that a legibility is decreased. In view of the above-described problem, the present invention aims at reducing the influence from the legibility decrease of the image based on the difference in the degree of the suppression on the correlative interference wave for each scanning line in a case where the FDI and the adaptive signal processing are applied.

Solution to Problem

A subject information obtaining apparatus according to an aspect of the present invention is a subject information obtaining apparatus that receives an elastic wave from a subject and obtains information on the subject, the apparatus including: a plurality of conversion elements configured to convert the elastic wave into a plurality of reception signals; a delay and sum unit configured to perform a delay and sum process by using the plurality of reception signals and output a plurality of scanning line signals; a scanning line synthesis unit configured to add the plurality of scanning line signals between adjacent scanning lines and output a plurality of synthesis scanning line signals; and an FDI adaptive processing unit configured to perform a frequency domain interferometry and an adaptive signal processing by using the plurality of synthesis scanning line signals and obtain a power intensity distribution.

In addition, a subject information obtaining method according to another aspect of the present invention is a subject information obtaining method of receiving an elastic wave from a subject and obtaining information on the subject, the method including: performing a delay and sum process by using a plurality of reception signals output from a plurality of conversion elements that receive the elastic wave and outputting a plurality of scanning line signals; adding the plurality of scanning line signals between adjacent scanning lines and outputting a plurality of synthesis scanning line signals; and performing a frequency domain interferometry and an adaptive signal processing by using the plurality of synthesis scanning line signals and obtaining a power intensity distribution.

Advantageous Effects of Invention

According to the aspect of the present invention, it is possible to reduce the influence from the legibility decrease of the image based on the difference in the degree of the suppression on the correlative interference wave for each scanning line.

DESCRIPTION OF EMBODIMENTS

A description will be provided of embodiments of the present invention with reference to the drawings. According to the embodiments of the present invention, an elastic wave is typically an ultrasonic wave and includes elastic waves referred to as sound wave, ultrasonic wave, and acoustic wave. A subject information obtaining apparatus according to the embodiments of the present invention includes an apparatus configured to transmit an elastic wave to a subject and receive a reflection wave reflected within the subject (reflected elastic wave) to obtain subject information as image data. The subject information to be obtained is information that reflects a difference in an acoustic impedance of tissues located inside the subject. In addition, a scanning line according to the embodiments of the present invention means a virtual line formed in a travelling direction of the elastic wave transmitted from a probe.

Basic Configuration of Subject Information Obtaining Apparatus

Figure 1:
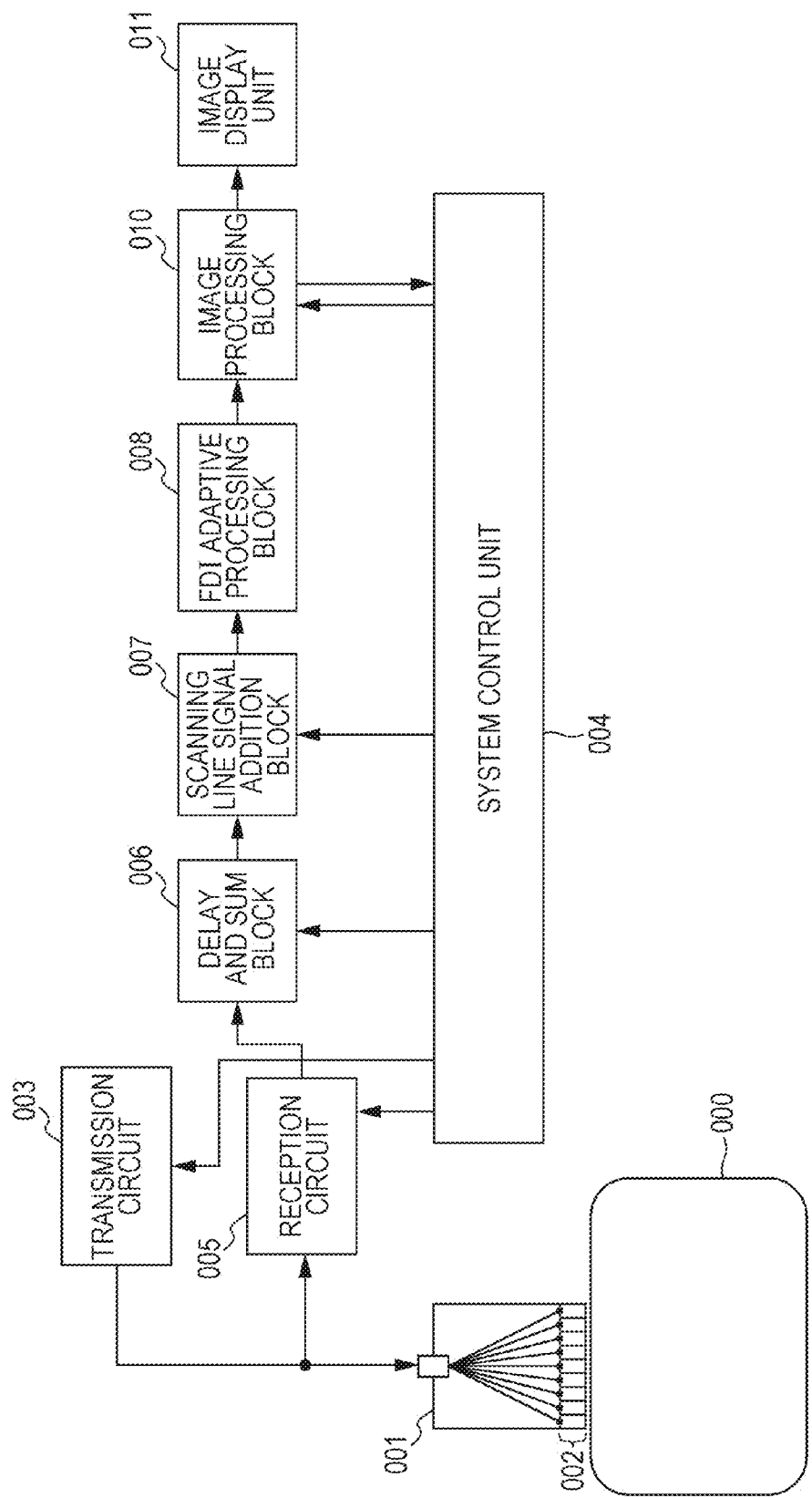
FIG. 1 is a schematic diagram of a system outline of a subject information obtaining apparatus to which an embodiment of the present invention can be applied.
Figure 2:
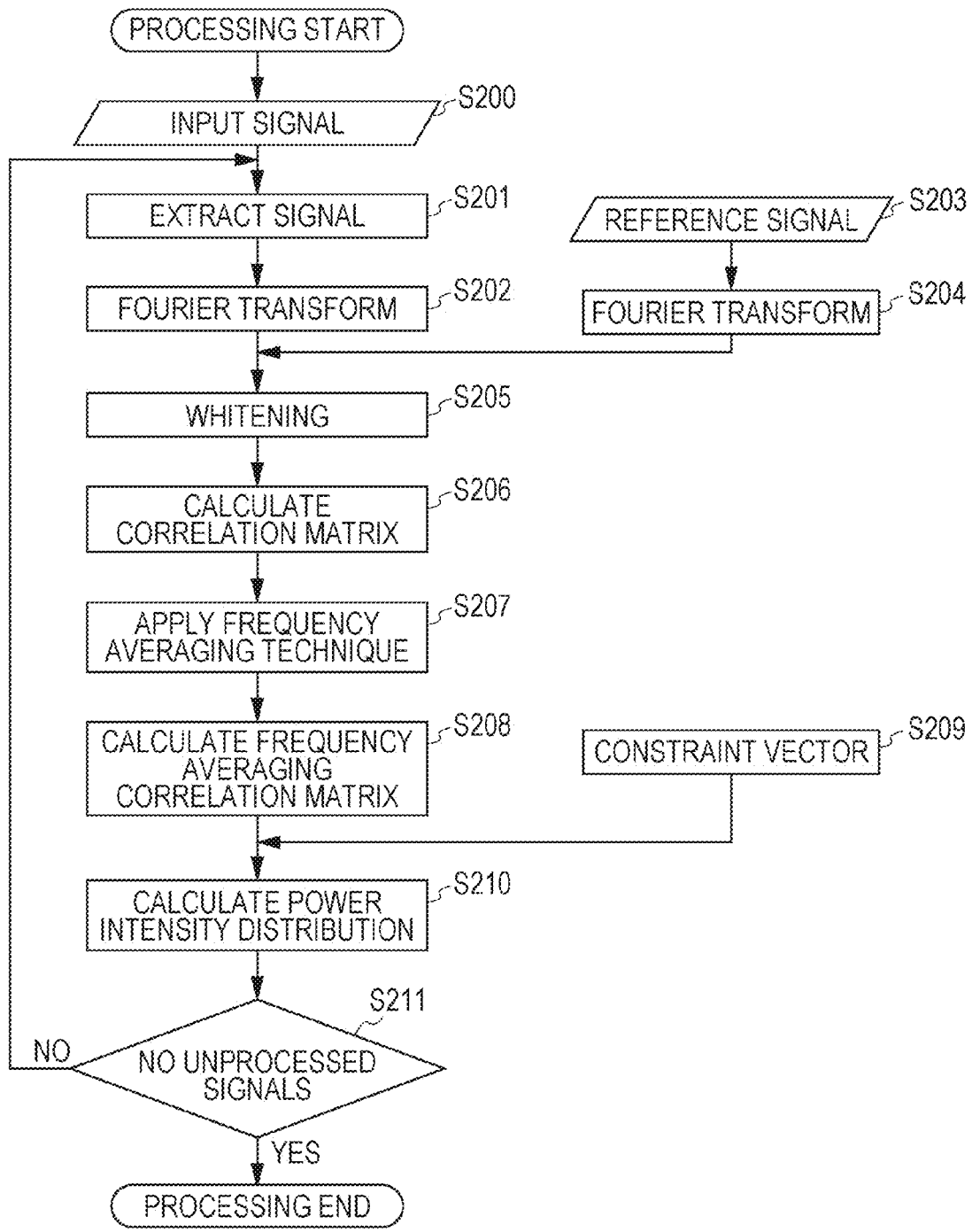
FIG. 2 is a flow chart for describing a processing within an FDI adaptive processing block.

A configuration of a subject information obtaining apparatus to which an embodiment of the present invention can be applied and a processing content at a time when an FDI and an adaptive signal processing are used will be described by using FIG. 1 and FIG. 2. FIG. 1 is a schematic diagram of a system outline of the subject information obtaining apparatus according to the embodiment of the present invention. The subject information obtaining apparatus according to the present embodiment of the present invention is provided with a probe 001 having plural conversion elements 002, a reception circuit 005, a transmission circuit 003, a delay and sum block 006, a scanning line signal addition block 007, an FDI adaptive processing block 008, an image processing block 010, and a system control unit 004.

According to the embodiment of the present invention, the delay and sum block 006 is equivalent of a delay and sum unit, the scanning line signal addition block 007 is equivalent of a scanning line signal synthesis unit, the FDI adaptive processing block 008 is equivalent of an FDI adaptive processing unit, and the image processing block 010 is equivalent of an image processing unit. Also, a processing apparatus is constructed at least by the delay and sum block 006, the scanning line signal addition block 007, and the FDI adaptive processing block 008. The processing apparatus may be further provided with an inter-scanning line shift amount estimation block 009 as a shift amount calculation unit (see FIG. 4 of a first exemplary embodiment) or the like as appropriate.

The transmission circuit 003 generates a transmission signal having a delay time and an amplitude in accordance with a focus position and a focus direction while following a control signal from the system control unit 004. This transmission signal is converted into an elastic wave by the plural conversion elements 002 and transmitted from the probe 001 to a subject. The elastic wave (reflection wave) reflected within a subject 000 is received by the plural conversion elements 002 and converted into plural reception signals. The reception signals are input to the reception circuit 005. In the reception circuit 005, the plural reception signals are amplified and converted into plural digital signals (digitalized reception signals). Herein, according to the embodiment of the present invention, not only analog reception signals that are output by the conversion elements 002 but also signals on which the processing such as the amplification or the digital conversion is carried out are also represented as reception signals.

The plural digital signals output from the reception circuit 005 are input to the delay and sum block 006. In the delay and sum block 006, in accordance with the direction and the position where the elastic wave is transmitted, the delay processing on the plural digital signals is carried out and then to be added, to elaborate, the execution of the delay and sum process. The plural signals thus subjected to the delay and sum process (scanning line signals) are input to the scanning line signal addition block 007. Plural scanning line signals are disposed on a single scanning line. A B-mode image displayed by the general ultrasonic diagnosis apparatus is obtained by disposing an envelope of this scanning line signal for plural scanning lines.

In the scanning line signal addition block 007, mutual scanning line signals on adjacent scanning lines (including continuously adjacent plural scanning line signals) are added, and a synthesis scanning line signal is output. Since this scanning line signal input to the scanning line signal addition block 007 does not obtain an envelope, phase information on a reception signal waveform is held. In addition, the synthesis scanning line signal output from the scanning line signal addition block 007 also holds phase information.

The above-described synthesis scanning line signal is input to the FDI adaptive processing block 008. Frequency domain interferometry (FDI) is a method of decomposing the reception signal for each frequency and changing a phase of the decomposed signal in accordance with a focus position to estimate a reception power at the focus position. It is noted that a phase change amount can be previously decided from a product of a distance from a certain reference position to the focus position and a wave number corresponding to the frequency.

Also, in the adaptive signal processing, a processing parameter thereof is adaptively changed in accordance with the reception signal. The Capon technique which is one of the adaptive signal processings is a method of processing plural input signals so as to minimize the power in a state in which a sensitivity related to a focus position is fixed. To elaborate, according to a combination of the FDI and the adaptive signal processing, with respect to the reception signal decomposed into the respective frequency components, the reception power at the focus position is estimated by using the adaptive signal processing instead of the previously decided phase change amount and weight.

Flow of FDI Adaptive Processing to which the Embodiment of the Present Invention can be Applied Hereinafter, by using FIG. 2, a processing within the FDI adaptive processing block 008 will be described. The FDI adaptive processing block 008 receives the synthesis scanning line signal output from the scanning line signal addition block 007 as an input signal (S200). Then, synthesis scanning line signals for a time corresponding to a batch for a single process, to elaborate, signals for a processing range are extracted from the plural synthesis scanning line signals (S201). Herein, for the processing within the FDI adaptive processing block 008, not only the signals for the processing range are extracted from the plural synthesis scanning line signals, but also a processing such as weighting may be carried out on the respective synthesis scanning line signals. In the above-described case too, according to the embodiment of the present invention, it is represented that the FDI is applied to the synthesis scanning line signals.

Next, the extracted signal is subjected to Fourier transform and decomposed into a component for each frequency (Xs1, Xs2, Xs3, . . . , XsN) (S202).

On the other hand, a reference signal is input to the FDI adaptive processing block 008 from the system control unit (S203), Fourier transform on the reference signal is carried out to be divided into components for each frequency (Xr1, Xr2, Xr3, . . . , XrN) (S204). The reference signal is an assumed signal waveform of the reflection wave that is returned from a boundary surface existing inside the subject (for example, a vessel wall or the like) and is stored in the system control unit 004.

Next, the FDI adaptive processing block 008 performs a whitening processing represented by the following expression (S205).

$$X_{wk} = \frac{X_{sk} X_{rk}^*}{|X_{rk}|^2 + \eta} \quad \text{[Math. 1]}$$

Where $X_{wk}$ (k=1, 2, . . . N) denotes a component for each frequency after the whitening processing, $\eta$ denotes a minutely small amount for stability, and * means complex conjugate. By using a vector X composed of the respective frequency components on which the whitening processing is carried out, a correlation matrix R is calculated (S206).

$$X=[X_{W1}, X_{W2}, \ldots, X_{WN}]^T R=XX^{T*}$$

It is noted that T means transposition. Where the correlation matrix R is a matrix having a size of N×N. Next, submatrices are extracted from the correlation matrix R, and a frequency averaging technique for averaging the submatrices is applied (S207).

$$R' = \frac{1}{M} \sum_{m=1}^{M} R_m \quad \text{[Math. 2]}$$

$$R_{mij} = X_{W(i+m-1)} X_{W(j+m-1)}^*$$

R' denotes a frequency averaging correlation matrix, and $R_m$ denotes a submatrix of the correlation matrix R having $R_{mij}$ as an element. In this manner, the frequency averaging correlation matrix R' is calculated (S208).

Figure 10:
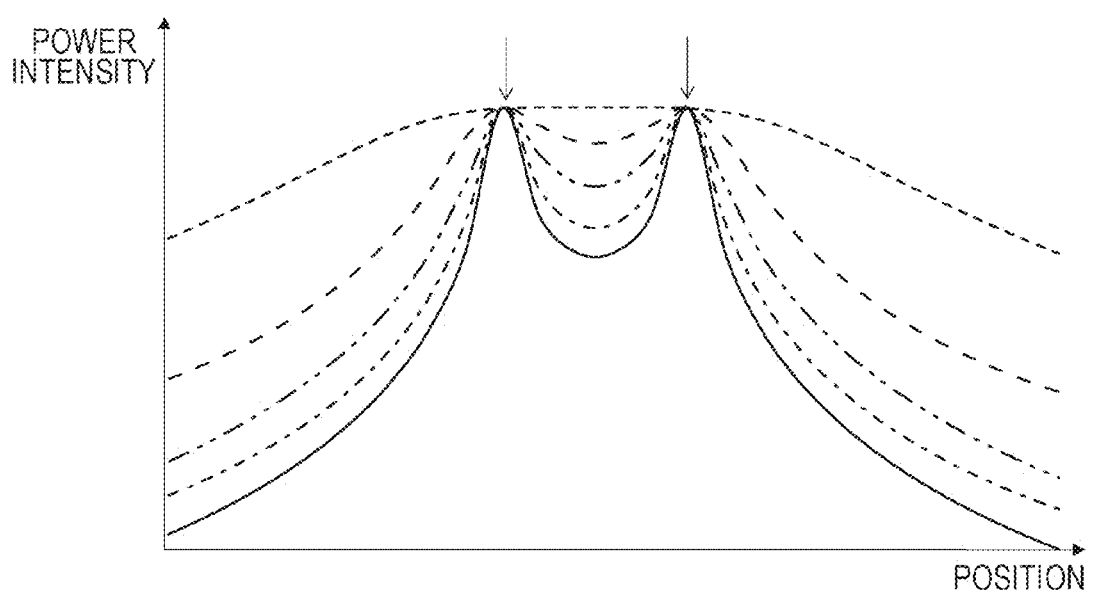
FIG. 10 illustrates a change in a power intensity distribution accompanied by a change in a submatrix size.

Here, a size of the submatrix $R_m$ in the frequency averaging technique. FIG. 10 illustrates a change in a power intensity distribution by the FDI and the Capon technique accompanied by a change in the size of the submatrix. A horizontal axis of FIG. 10 represents a position in a travelling direction of the elastic wave (to elaborate, a scanning line direction), and a vertical axis represents a power intensity distribution. The FDI and the Capon technique are applied to the reception signals of the reflection waves from two-layer reflection surfaces arranged at an interval of 0.05 mm, and results of changing the submatrix size at that time are represented by plural plots.

It is noted that the two-layer reflection surfaces exist at two locations indicated by arrows in FIG. 10. Also, the plural plots in FIG. 10 illustrate the power intensity distributions in a case where a size of the submatrix is set as 17 (dotted line), 131 (broken line), 51 (dashed-two dotted line), 119 (dashed-dotted line), and 85 (solid line) with respect to a correlation matrix size N=134. From FIG. 10, it is found out that the spatial resolution is changed as the size of the submatrix is changed.

Figure 11:
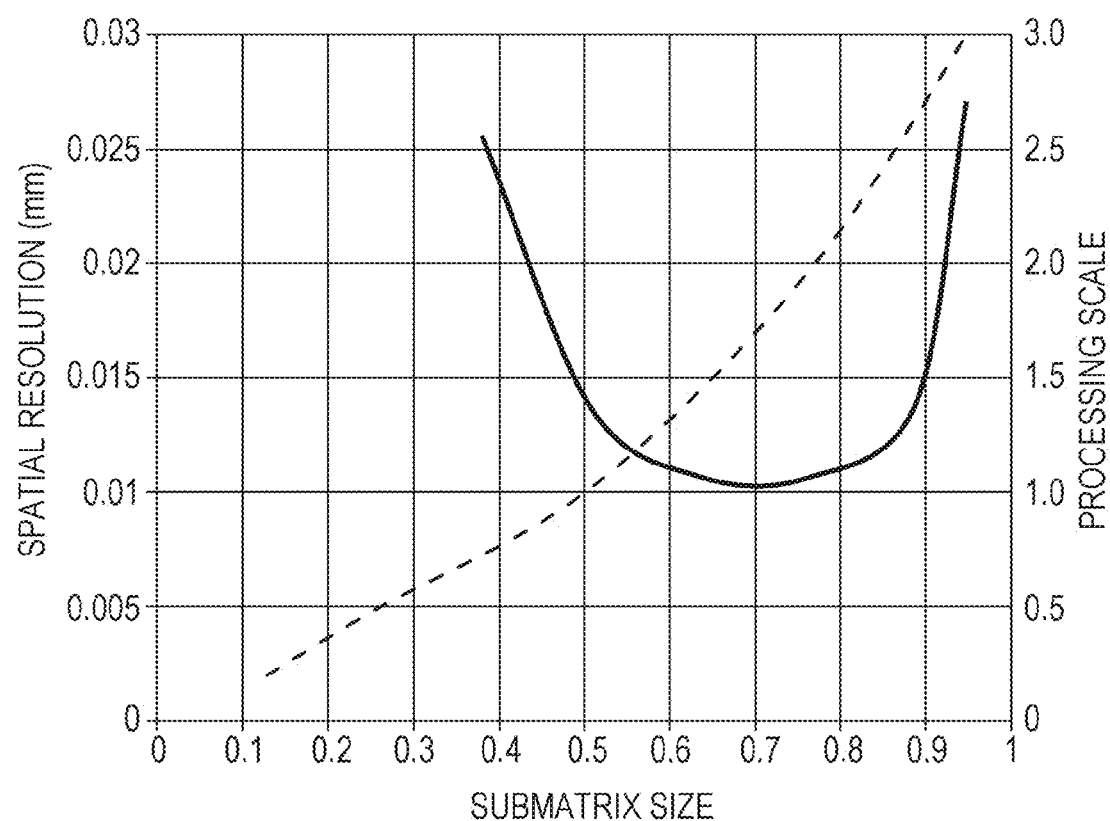
FIG. 11 illustrates changes in a spatial resolution and a processing scale accompanied by the change in the submatrix size.

FIG. 11 illustrates changes in a spatial resolution and a processing scale accompanied by a change in the submatrix size. A horizontal axis represents a size of the normalized submatrix when the correlation matrix size is set as 1, and vertical axes represent a change in the spatial resolution (solid line) and a processing calculation scale (broken line) at the respective submatrix sizes. It is noted that the processing calculation scale is normalized to be set as 1 when the submatrix size is 0.5.

From FIG. 11, it is found out that the maximum spatial resolution can be obtained when the submatrix size is in the vicinity of 0.5 to 0.9. On the other hand, it is found out that since the processing scale is abruptly increased as the submatrix size is increased, in particular, when the submatrix size exceeds approximately 0.8, the processing scale is increased, but the spatial resolution is degraded. In addition, the spatial resolution is abruptly degraded in an area where the submatrix size is lower than or equal to 0.3. From these findings, the size of the submatrix is preferably 0.3 or higher, and furthermore, to suppress the increase in the calculation scale, 0.8 or lower is preferably selected. Also, furthermore, to obtain a high spatial resolution at an appropriate processing scale, the submatrix size is preferably in a range higher than 0.5 and lower than or equal to 0.8, and the size of the submatrix may be decided depending on which of the spatial resolution or the processing scale a high priority is given to.

Next, a constraint vector C is input to the FDI adaptive processing block 008 (S209). The constraint vector C is a vector changing in accordance with a position r in the processing range and is defined by the following expression.

$$C=[\exp(jk_1 r), \exp(jk_2 r), \ldots, \exp(jk_{(N-M+1)} r)]$$

By using the frequency averaging correlation matrix R' and the constraint vector C, the power intensity distribution P(r) in the processing range is calculated (S210).

$$P(r) = \frac{1}{C^{T*}(R' + \eta' E)^{-1} C} \quad \text{[Math. 3]}$$

η'E denotes a diagonal matrix added for stabilizing an inverse matrix calculation.

Furthermore, among the input signals, if an unprocessed signal does not exist, the processing is ended, and if the unprocessed signal exists, the flow is returned to the signal extraction (S201), and the processing is continued (S211).

In this manner, in the FDI adaptive processing block 008, the FDI and the adaptive signal processing (herein, the Capon technique is used) are carried out while the synthesis scanning line signal output from the scanning line signal addition block 007 is used as the input signal, and the power intensity distribution is output. According to the embodiment of the present invention, the obtained power intensity distribution indicates the subject information that reflects the difference in the acoustic impedance of the tissue within the subject.

While the power intensity distribution output from the FDI adaptive processing block 008 is used as input information, the image processing block 010 performs various image processings such as the edge emphasis and the contrast adjustment while following the instruction from the system control unit 004 and outputs luminance data (image data). An image display unit 011 displays the input luminance data as an image. It is noted that the image display unit 011 may be provided separately aside the subject information obtaining apparatus according to the embodiment of the present invention.

Processing of Scanning Line Signal Addition Block

Here, a concept of an operation in the scanning line signal addition block 007 which is carried out in a stage previous to the FDI adaptive processing block 008 will be described by using FIG. 3.

Figure 3:
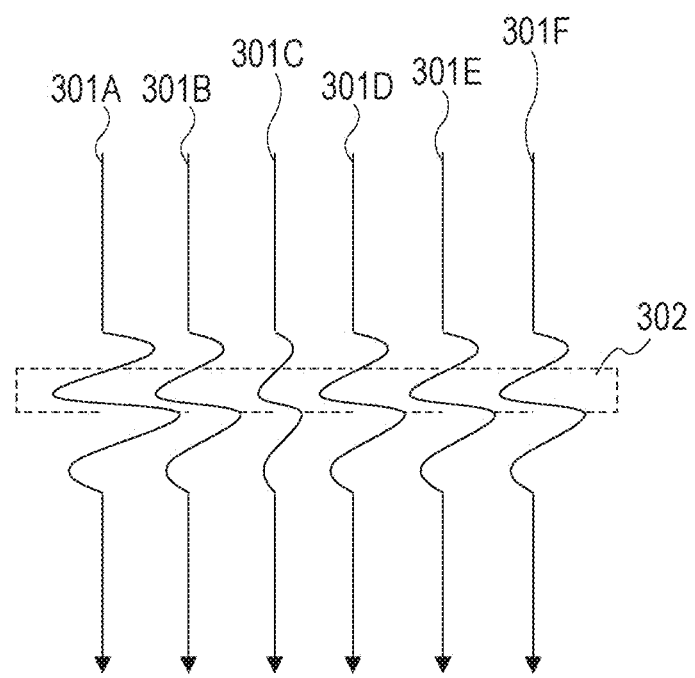
FIG. 3 schematically illustrates plural scanning line signals.

FIG. 3 schematically illustrates scanning line signals 301A to 301F on the scanning lines. As described above, in the B-mode image (image generated by obtaining the envelope of the scanning line signal) generated by the general ultrasonic diagnosis apparatus, the spatial resolution in the direction intersecting with the scanning line (lateral direction in FIG. 3) is larger (longer) than a distance between the scanning lines.

To elaborate, a change in the scanning line signal in the direction intersecting with the scanning line (for example, a part denoted by reference sign 302) is a smooth change. An intensity change in the direction intersecting with the scanning line when the envelope of the scanning line signal is obtained is also a smooth change.

However, in a case where the FDI and the adaptive signal processing are used, since the degree of the suppression on the correlative interference wave varies for each scanning line, a continuity of the power intensity in the direction intersecting with the scanning line may be lowered. In view of the above, the scanning line signal addition block 007 adds the scanning line signals on the plural adjacent scanning lines (for example, 301B, 301C, and 301D) to be output as a new synthesis scanning line signal. According to this, the continuity in the direction intersecting with the scanning line can be increased. In addition, since an SN ratio of the signal is improved by this addition, it is possible to enhance the effect of the resolution improvement by the FDI and the adaptive signal processing.

By carrying out the above-described processing, not only the effect of the improvement in the spatial resolution in the scanning line direction by using the FDI and the adaptive signal processing can be obtained, but also the influence from the continuity decrease of the image by the difference in the degree of the suppression on the correlative interference wave for each scanning line can be suppressed. Therefore, it is possible to obtain the more stable image data having the high legibility.

It is noted that herein, the processing of the Capon technique has been described as an example of the adaptive signal processing, but the effect of the embodiment of the present invention can be similarly obtained also in another adaptive signal processing where the frequency averaging technique is employed to suppress the influence of the correlative interference wave, a MUSIC technique, an ESPRIT technique, and the like.

Hereinafter, the subject information obtaining apparatus according to the embodiments of the present invention will be described in detail by using the drawings. It is noted that same components are assigned with the same reference signs in principle, and a description there of will be omitted.

First Exemplary Embodiment

Figure 4:
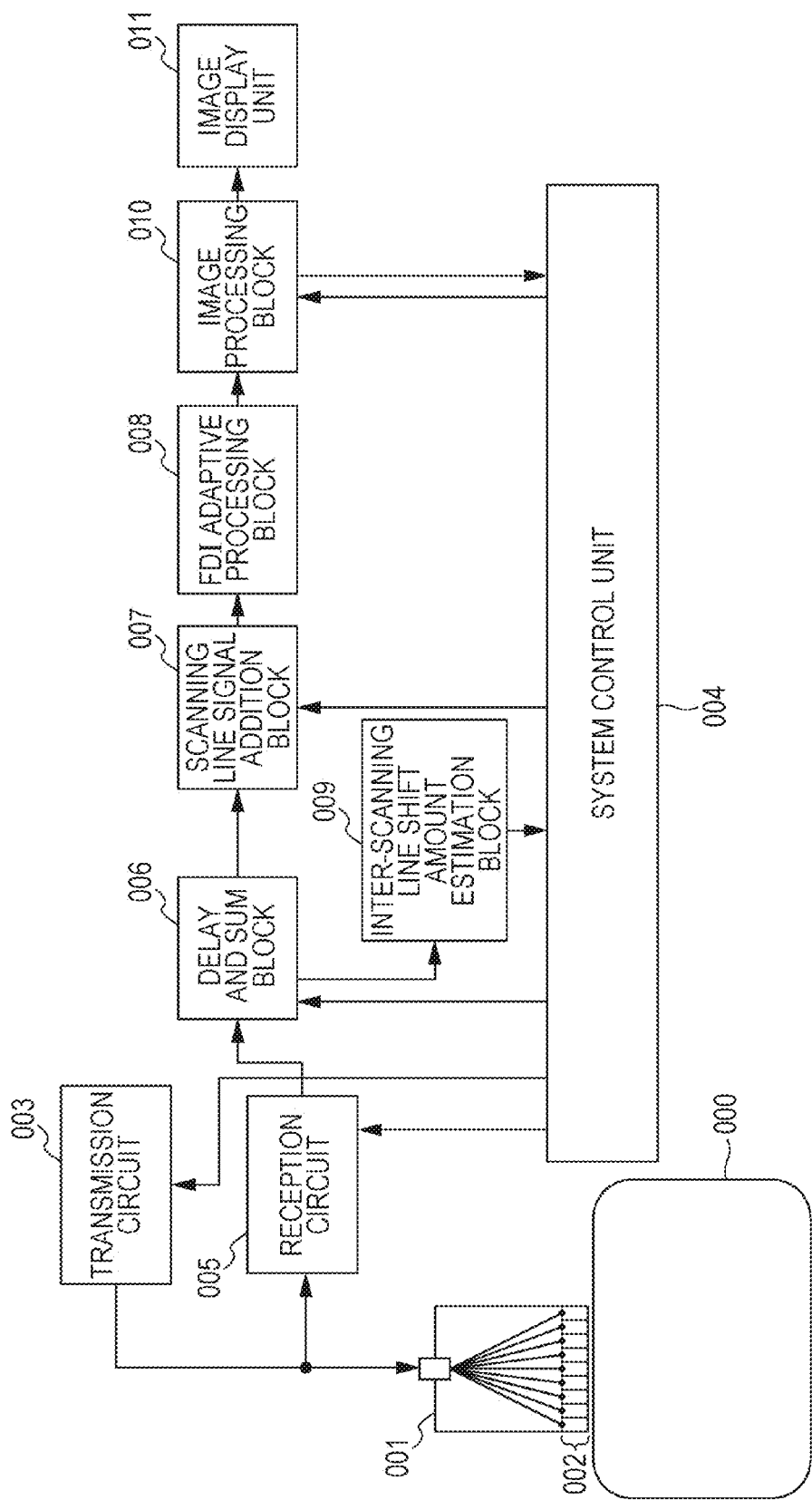
FIG. 4 is a schematic diagram of a system outline according to a first exemplary embodiment.

A first exemplary embodiment of the present invention will be described by using FIG. 4 to FIGS. 8A to 8D. FIG. 4 is a system schematic diagram of the subject information obtaining apparatus used in the present embodiment.

Basic Apparatus Configuration of First Exemplary Embodiment

The subject information obtaining apparatus according to the present embodiment is provided with the inter-scanning line shift amount estimation block 009 in addition to the respective components illustrated in FIG. 1. According to the present embodiment, the delay and sum block 006 is equivalent of the delay and sum unit, the inter-scanning line shift amount estimation block 009 is equivalent of the shift amount calculation unit, and the scanning line signal addition block 007 is equivalent of the scanning line signal synthesis unit. In addition, the FDI adaptive processing block 008 is equivalent of the FDI adaptive processing unit, and the image processing block 010 is equivalent of the image processing unit. It is noted that according to the present embodiment, the processing apparatus is structured by the delay and sum block 006, the inter-scanning line shift amount estimation block 009, the scanning line signal addition block 007, and the FDI adaptive processing block 008.

The transmission circuit 003 generates a transmission signal having a delay time and an amplitude in accordance with a focus position and a focus direction while following a control signal from the system control unit 004. This transmission signal is converted into an elastic wave by the plural conversion elements 002 and transmitted from the probe 001 into the subject. The elastic wave (reflection wave) reflected within the subject 000 is received by the plural conversion elements 002. The reception signals are input to the reception circuit 005.

In the reception circuit 005, the plural reception signals are amplified and converted into plural digital signals. The plural digital signals output from the reception circuit 005 are input to the delay and sum block 006.

In the delay and sum block 006, in accordance with the direction and the position where the elastic wave is transmitted, an addition is carried out after a delay processing on the plural digital signals, to elaborate, a delay and sum process is executed. The plural signals thus subjected to the delay and sum process are input to the inter-scanning line shift amount estimation block 009 as the scanning line signals. The B-mode image displayed by the general ultrasonic diagnosis apparatus is obtained by disposing the envelope of this scanning line signal.

The inter-scanning line shift amount estimation block 009 calculates the power intensity distributions of the respective scanning lines through the FDI and the adaptive signal processing with respect to the input scanning line signal and calculates a shift amount for each scanning line at a target position. A detail thereof will be described below by using FIGS. 5A and 5B to FIG. 7, but the inter-scanning line shift amount estimation block 009 calculates a shift amount at the target position between the scanning lines for each area within the subject and outputs information on the shift amount to the system control unit 004.

The scanning line signal addition block 007 performs a synthesis processing on the scanning line signals by shifting the input scanning line signal to be added on the basis of the scanning line signal input from the delay and sum block 006 and the shift amount at the target position for each scanning line input from the system control unit 004. The synthesis scanning line signal output from the scanning line signal addition block 007 is input to the FDI adaptive processing block 008.

While the synthesis scanning line signal output from the scanning line signal addition block 007 is used as an input signal, the FDI adaptive processing block 008 performs the FDI and the adaptive signal processing and outputs the power intensity distribution.

While the power intensity distribution output from the FDI adaptive processing block 008 is used as the input, the image processing block 010 performs various image processings such as the edge emphasis and the contrast adjustment while following the instruction from the system control unit 004 and outputs the luminance data. The image display unit 011 displays the input luminance data.

Basic Processing Flow of First Exemplary Embodiment

Figure 7:
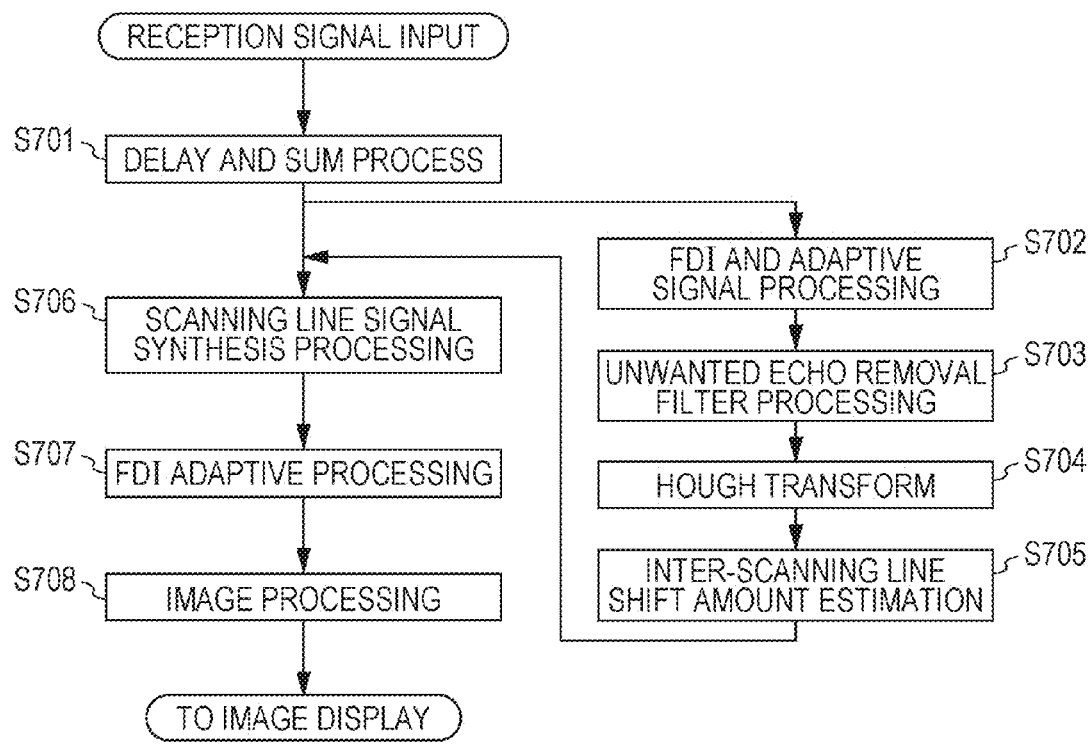
FIG. 7 is a flow chart for describing a flow of a processing according to the first exemplary embodiment.

A flow of the subject information obtaining method according to the present embodiment will be described by using FIG. 7. The flow of FIG. 7 starts from a step in which a digitalized reception signal (digital signal) is input.

In S701, in accordance with the direction and the position where the elastic wave is transmitted, the delay and sum block 006 performs the delay processing on the plural digital signals to be added, to elaborate, the delay and sum process is executed.

In S702, the inter-scanning line shift amount estimation block 009 performs a processing of calculating the power intensity distributions of the respective scanning lines through the FDI and the adaptive signal processing with respect to the input signal after the delay and sum (the scanning line signal). By disposing this power intensity distribution, a luminance value data group having a high resolution as compared with a B-mode image in a general ultrasonic apparatus is constructed.

Furthermore, in S703, the inter-scanning line shift amount estimation block 009 applies an unwanted echo removal filter to this luminance value data group. This filter processing is a processing of obtaining a power intensity distribution IB(z) after the unwanted echo removal when the power intensity distribution of the scanning line is set as I(z) as follows.

$$I_M(z1) = \max_{z0 \leq z \leq z1} I(z) \quad [\text{Math. 4}]$$

$$I_B(z1) = \begin{cases} 0 & \text{when } I(z1) < I_M(z1 - zm) \\ I(z1) - I_M(z1 - zm) & \text{else} \end{cases} \quad [\text{Math. 5}]$$

Where z0 denotes a starting point of a focus range, zm denotes a parameter which can be arbitrarily set, and zm is preferably set in a range of a depth resolution.

This unwanted echo removal filter processing is a filter processing of leaving a luminance value at the focus position in a case where the luminance value existing at the focus position has a luminance value higher than a high luminance value part existing at a position shallower than the depth of the target position (position close to the probe) and setting the other parts as 0. For example, in a case where this filter processing is applied to a power intensity distribution at a back wall part of the blood vessel, it is possible to obtain a luminance value data group where only two layers including a boundary between the intravascular lumen and the tunica media complex and a boundary between the internal media complex and the outer membrane exist.

Next, in S704, the inter-scanning line shift amount estimation block 009 divides the luminance value data group to which this unwanted echo removal filter is applied into plural areas and performs the Hough transform on each divided area. These plural areas are areas for plural scanning lines in a certain depth range. Through this Hough transform, a direction and a position of a part having a luminance value higher than or equal by a certain value are extracted. The certain value (threshold) used at this time may be changed for each scanning line, or a single threshold may be used for the entire areas to simplify the processing.

Figure 5A:
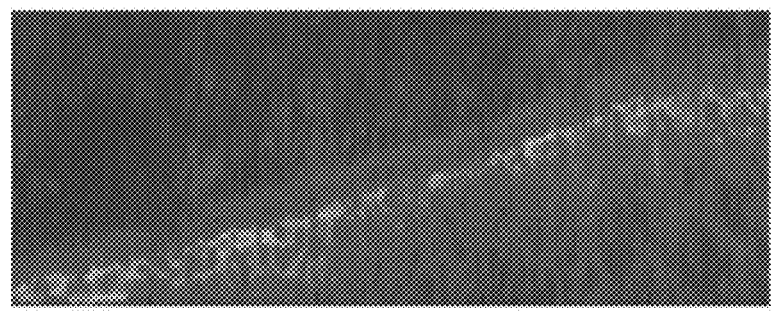
FIGS. 5A and 5B illustrate positions and directions extracted by Hough transform.
Figure 5B:
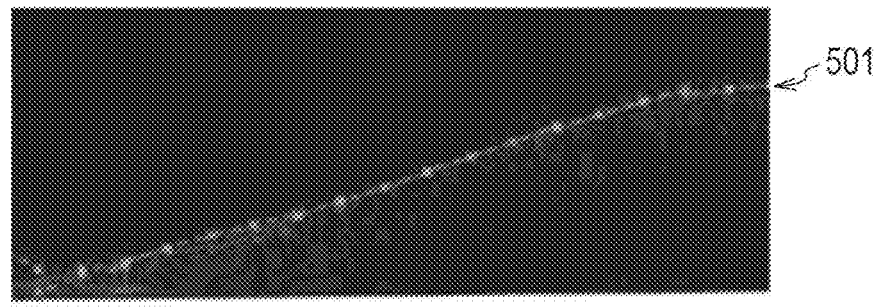

FIGS. 5A and 5B illustrate results after the Hough transform is carried out in the inter-scanning line shift amount estimation block 009. FIG. 5A illustrates an image where the unwanted echo removal filter is applied to the luminance value data group obtained by disposing the power intensity distribution calculated through the FDI and the adaptive signal processing. For the reception signal used at this time, a reception signal obtained while the carotid artery is targeted is used. FIG. 5B illustrates an image where the Hough transform is carried out in the luminance value data group illustrated in FIG. 5A. A line 501 of FIG. 5B represents a direction and a position of the line formed by the luminance value data group extracted for each area.

In this manner, according to the present embodiment, the direction and the position of the line formed by the luminance value data group are extracted through the Hough transform, but the effect of the embodiment of the present invention can also be obtained by using another algorithm such as a differential computation or a template matching.

The operation by the inter-scanning line shift amount estimation block 009 will be described again. In S705, the inter-scanning line shift amount estimation block 009 calculates how much the structure within the subject is shifted for each scanning line on the basis of the extracted direction and the position of the line formed by the luminance value data group. For example, how much the blood vessel wall is inclined is calculated. If an extracted angle is 30 degrees, and a distance between the scanning lines is 0.15 mm, the calculation is conducted to find out the shift amount of 86.6 µm. In this manner, the inter-scanning line shift amount estimation block 009 calculates the shift amount at the target position for each scanning line for each area and outputs information on the shift amount to the system control unit 004. The target position according to the present embodiment represents a line for each area formed by the luminance value data group extracted by applying the unwanted echo removal filter. This means that a position candidate of a measurement target matter (reflection boundary surface) within the subject such as a layer-like structure within the subject or a boundary where the acoustic impedance is changed. For example, in a case where the measurement target matter is a rectilinear blood vessel wall, the shift amount at the target position reflects an inclination of the blood vessel wall.

In S706, the scanning line signal addition block 007 performs the synthesis processing of shifting the scanning line signal in the scanning line direction to be added on the basis of the scanning line signal input from the delay and sum block 006 and the shift amount at the target position for each scanning line input from the system control unit 004.

Figure 6A:
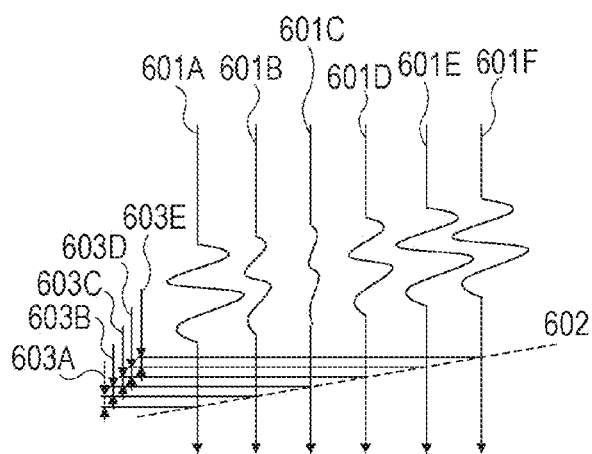
FIGS. 6A and 6B are schematic diagrams for describing an operation of a scanning line signal synthesis block.
Figure 6B:
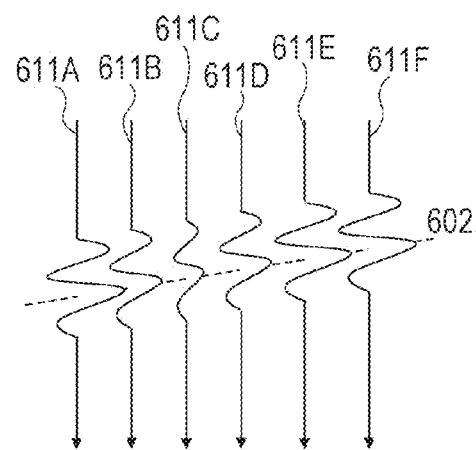

FIGS. 6A and 6B illustrate a concept of the synthesis processing of shifting the scanning line signal to be added. FIG. 6A illustrates plural scanning line signals before the synthesis processing, and FIG. 6B illustrates plural synthesis scanning line signals after the synthesis processing. Shift amounts 603A to 603E are shift amounts obtained from a direction 602 extracted in an area where the scanning line signal exists in S702 to S705.

The scanning line signal addition block 007 corrects scanning line signals 601A to 601F on the input scanning line by the shift amounts 603A to 603E. Then, the adjacent scanning line signals are added to each other. For example, among synthesis scanning line signals 611A to 611F, the synthesis scanning line signal 611B will be described. The synthesis scanning line signal 611B is obtained by adding a signal obtained by shifting the scanning line signal 601A in a deeper direction by the shift amount 603A (upwards in FIGS. 6A and 6B) and a signal obtained by shifting the scanning line signal 601B and the scanning line signal 601C in a shallower direction by the shift amount 603B (downwards in FIGS. 6A and 6B).

In the above-described example, the example has been made in which by using the two scanning line signals (601A and 601C) adjacent to the scanning line signal 601B, the shift is conducted for the three scanning line signals for the addition to calculate the synthesis scanning line signal 611B, but the present invention is not limited to this. The effect of the embodiment of the present invention can be obtained if the number of the synthesized scanning line signals is two or more. Furthermore, a weight may be applied at the time of the addition.

According to the embodiment of the present invention, to suppress the degradation of the spatial resolution in the direction intersecting with the scanning line, the addition is preferably carried out with the number of scanning lines lower than or equal to twice as many as the spatial resolution. In addition, the number of scanning lines is more preferably lower than or equal to the spatial resolution. It is noted that since the spatial resolution in the direction intersecting with the scanning line varies also depending on the depth to be observed, the used frequency, the size of the probe, and the like, the number to be added is preferably changed in accordance with those conditions.

The synthesis scanning line signal output from the scanning line signal addition block 007 is input to the FDI adaptive processing block 008. In S707, while the synthesis scanning line signal output from the scanning line signal addition block 007 is used as the input signal, the FDI adaptive processing block 008 performs the FDI and the adaptive signal processing and outputs the power intensity distribution.

In S708, while the power intensity distribution output from the FDI adaptive processing block 008 is used as the input, the image processing block 010 performs various image processings such as the edge emphasis and the contrast adjustment while following the instruction from the system control unit 004 and outputs the luminance data. The image display unit 011 displays the input luminance data.

Figure 8A:
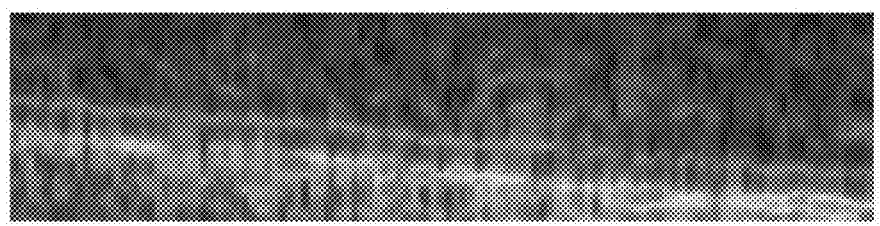
FIGS. 8A to 8D illustrate processing results according to the first exemplary embodiment.
Figure 8B:
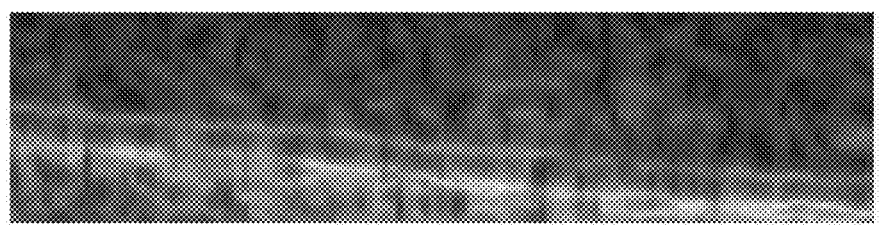
Figure 8C:
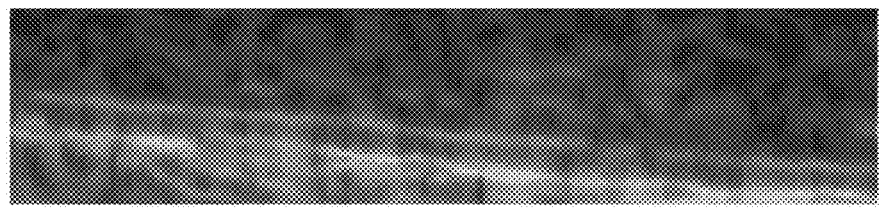
Figure 8D:
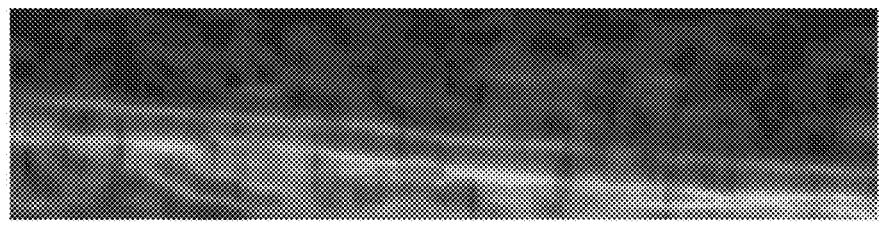

FIGS. 8A to 8D illustrate images representing results when the processing according to the present embodiment is applied. FIG. 8A illustrates a related art image obtained when the present invention is not applied and the processing is carried out by using the FDI and the adaptive signal processing. FIG. 8B illustrates an image obtained when the adjacent three scanning lines are used and the FDI and the adaptive signal processing is carried out on the synthesis scanning line signal shifted by the respective shift amounts to be added. FIG. 8C illustrates an image obtained when the adjacent five scanning lines are used and the FDI and the adaptive signal processing is carried out on the synthesis scanning line signal shifted by the respective shift amounts to be added. FIG. 8D illustrates an image obtained when the adjacent seven scanning lines are used and the FDI and the adaptive signal processing is carried out on the synthesis scanning line signal shifted by the respective shift amounts to be added. It is found out that with the application of the embodiment of the present invention, the continuity in the direction intersecting with the scanning line (the lateral direction of FIGS. 8A to 8D) is improved, and the legibility is increased.

According to the present embodiment, the shift amount between the scanning lines is estimated by using the luminance value data group where the scanning line signal is applied with the FDI and the adaptive signal processing, but the shift amount between the scanning lines can also be estimated by using the luminance value data group (the B-mode image) obtained by disposing the envelope of the scanning line signal.

In addition, the present invention is not limited to the mode in which the shift amount between the scanning lines is estimated, and the addition is conducted after the shift by the shift amount as in the present embodiment. As described by using FIG. 3, the addition may be conducted without the shift of the plural adjacent scanning line signals. This is because depending on the measurement target matter, a case also exists in which the measurement target matter is hardly inclined (to elaborate, the measurement target matter is substantially in parallel to the direction orthogonal to the scanning line). Therefore, in the above-described case, the FDI and the adaptive signal processing may be applied to the synthesis scanning line signal obtained by adding the simply adjacent scanning line signals.

Also, in the inter-scanning line shift amount estimation block 009, in an area where the direction and the position of the part in which the luminance value is high to a certain degree are not obtained or an accuracy thereof is considered to be low, it is also possible to directly carry out the processing of adding the scanning line signals without performing the processing of shifting the scanning line signal. To elaborate, a single image may be generated while the processing is carried out separately in a case where the processing of shifting the scanning line signal for each area is conducted and a case in which the processing of shifting the scanning line signal for each area is not conducted. By selecting the above-described processing, an unwanted movement of the scanning line signal in a part with a low luminance value or an area where reflectors randomly exist is avoided, and it is possible to obtain a stable image.

Second Exemplary Embodiment

Next, a second exemplary embodiment of the present invention will be described. According to the present embodiment, a method of estimating the shift amount at the target position for each scanning line is different from the first exemplary embodiment. The subject information obtaining apparatus according to the present embodiment is similar to the first exemplary embodiment described by using FIG. 4, but a function of the inter-scanning line shift amount estimation block 009 is different. Therefore, a processing flow part different from the first exemplary embodiment will be mainly described.

Figure 9:
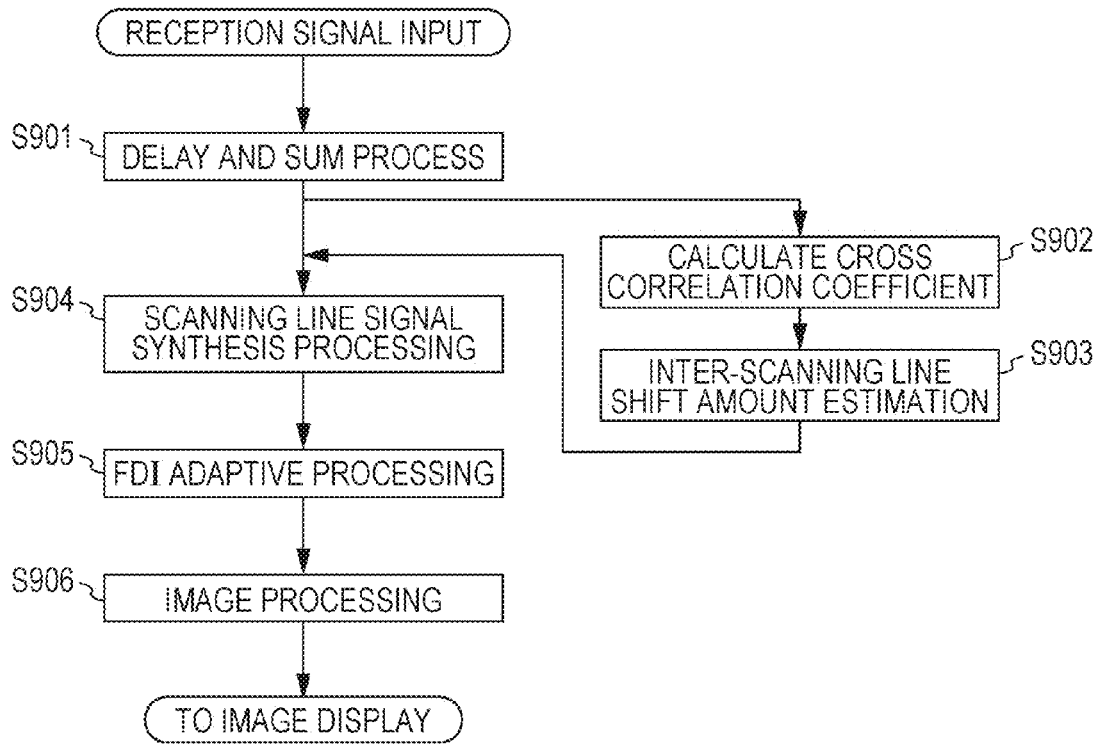
FIG. 9 is a flow chart for describing a flow of a processing according to a second exemplary embodiment.

A flow of the subject information obtaining method according to the present embodiment will be described by using FIG. 9. The flow of FIG. 9 starts from a step in which a digitalized reception signal (digital signal) is input. In S901, the delay and sum block 006 performs a delay and sum process while the plural digital signals are used as inputs. The signals thus subjected to the delay and sum process are input to the inter-scanning line shift amount estimation block 009 as the scanning line signals.

In S902, the inter-scanning line shift amount estimation block 009 cuts off the adjacent scanning line signals at every certain depth and calculates a cross correlation coefficient r(k) of those.

$$r(k) = \frac{\sum_{i=1}^{n-k} x_i y_{i+k}}{\sqrt{\sum_{i=1}^{n-k} x_i^2} \sqrt{\sum_{i=1}^{n-k} y_{i+k}^2}}$$ [Math. 6]

Where $x_i$ and $y_i$ denote respective signal strings cut off from the scanning line signals (i=1, 2, 3, . . . , n). k denotes a shift amount for each scanning line.

In S903, the inter-scanning line shift amount estimation block 009 estimates a shift amount at the target position for each of the adjacent scanning lines at respectively cut-off depths on the basis of a value of k taking a maximum value of the cross correlation coefficient r(k). According to the present embodiment, the target position itself is not obtained from the luminance value data group like the first exemplary embodiment, but the shift amount at the target position for each scanning line is obtained by using the cross correlation coefficient. This shift amount at the target position reflects a shift of the position between the scanning lines of a measurement target matter within the subject (such as a layer-like structure continually existing across the plural scanning lines within the subject or a boundary where the acoustic impedance is changed). For example, in a case where the measurement target matter is the rectilinear blood vessel wall, the shift amount at the target position reflects the inclination of the blood vessel wall. In this manner, the inter-scanning line shift amount estimation block 009 calculates the shift amount for each scanning line for each area to be output to the system control unit 004.

It is noted that herein, the cross correlation coefficient between the adjacent scanning lines is used, but a cross correlation coefficient between the scanning line and the adjacent scanning line after the next (mutual scanning lines) may be used. In addition, an average value may also be used with respect to the plural shift amounts obtained from combinations of the plural mutual scanning lines. Furthermore, a more stable shift amount may be obtained by applying a technique of extracting a part with a low spatial frequency with regard to the direction orthogonal to the scanning line within the subject to suppress a sudden change in the shift amount due to an influence from noise or the like with respect to the plural shift amounts calculated over the combinations of the plural mutual scanning lines, for example.

In S904, the scanning line signal addition block 007 performs a synthesis processing on the scanning line signals for shifting the input scanning line signal to be added on the basis of the scanning line signal input from the delay and sum block 006 and the information on the shift amount for each scanning line input from the system control unit 004. The synthesis scanning line signal output from the scanning line signal addition block 007 is input to the FDI adaptive processing block 008.

In S905, while the synthesis scanning line signal output from the scanning line signal addition block 007 is used as the input signal, the FDI adaptive processing block 008 performs the FDI and the adaptive signal processing and outputs the power intensity distribution.

In S906, while the power intensity distribution output from the FDI adaptive processing block 008 is used as the input, the image processing block 010 performs various image processings such as the edge emphasis and the contrast adjustment while following the instruction from the system control unit 004 and outputs the luminance data. The image display unit 011 displays the input luminance data.

By using the present embodiment, the continuity in the direction intersecting with the scanning line (lateral direction) is improved, and the legibility is increased. Furthermore, according to the present embodiment, since the shift amount is calculated by using the cross correlation value of the scanning line signal, the shift amount between the scanning lines is estimated at a satisfactory accuracy, and the effect of the SN ratio improvement through the scanning line signal synthesis processing can be enhanced. For that reason, it is expected that the effect of the resolution improvement through the FDI and the adaptive signal processing can further be enhanced.

Also, in the inter-scanning line shift amount estimation block 009, in the area where the cross correlation value is not large up to a certain extent, it is also possible to carry out the processing of directly adding the scanning line signals without performing the processing of shifting the scanning line signal. By selecting the above-described processing, an unwanted movement of the scanning line signal in a part with a low luminance value or an area where reflectors randomly exist is avoided, and it is possible to obtain a further stable image.

Third Exemplary Embodiment

In addition, the embodiments of the present invention can also be realized by executing the following processing. That is, the processing is executed while software (program) that realizes the functions of the above-described respective embodiments is supplied to a system or an apparatus via a network or various storage media, and a computer (or a CPU, an MPU, or the like) of the system or the apparatus reads out the program for the execution.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-191416, filed Sep. 2, 2011, which is hereby incorporated by reference herein in its entirety.

REFERENCE SIGNS LIST 000 subject
001 probe
002 conversion element
003 transmission circuit
004 system control unit
005 reception circuit
006 delay and sum block
007 scanning line signal addition block
008 FDI adaptive processing block
009 inter-scanning line shift amount estimation block
010 image processing block
011 image display unit
301A to 301F scanning line signal
601A to 601F scanning line signal
611A to 611F synthesis scanning line signal

The invention claimed is:

1. A subject information obtaining apparatus that obtains information of a subject based on an elastic wave received from the subject, the subject information obtaining apparatus comprising:
a plurality of conversion elements configured to convert the elastic wave into a plurality of reception signals;
a delay and sum unit configured to perform a delay and sum process by using the plurality of reception signals output from the plurality of conversion elements and generate a first plurality of scanning line signals;
a scanning line synthesis unit;
an FDI (frequency domain interferometry) adaptive processing unit configured to perform a frequency domain interferometry and an adaptive signal processing by using the first plurality of scanning line signals and obtain a first power intensity distribution; and
a shift amount calculation unit configured to calculate a shift amount at a target position for each scanning line with the use of the first power intensity distribution,
wherein the scanning line synthesis unit shifts the first plurality of scanning line signals by using the shift amount and generates a second plurality of scanning line signals,
wherein the scanning line synthesis unit adds spatially adjacent two or more scanning line signals from the second plurality of scanning line signals and generates a plurality of synthesis scanning line signals, and
wherein the FDI adaptive processing unit performs the frequency domain interferometry and the adaptive signal processing by using the plurality of synthesis scanning line signals and generates a second power intensity distribution.

2. The subject information obtaining apparatus according to claim 1, wherein the scanning line synthesis unit adds the two or more scanning line signals with a weight.

3. The subject information obtaining apparatus according to claim 1, wherein a number of the first or second plurality of scanning line signals to be added is changed in accordance with at least one of a depth to be observed, a used frequency of the elastic wave, and a size of the plurality of conversion elements.

4. A subject information obtaining method of obtaining information of a subject based on an elastic wave received from the subject, the subject information obtaining method comprising:
performing a delay and sum process by using a plurality of reception signals output from a plurality of conversion elements that receive the elastic wave and generating a first plurality of scanning line signals;
performing, using the microprocessor, a frequency domain interferometry and an adaptive signal processing by using the first plurality of scanning line signals to generate a first power intensity distribution;
performing, using the microprocessor, a calculation process to calculate a shift amount at a target position for each scanning line with use of the first power intensity distribution;
performing, using the microprocessor, a shift process to shift the first plurality of scanning line signals by using the shift amount and generating a second plurality of scanning line signals;
performing, using the microprocessor, the scanning line synthesis process to add spatially adjacent two or more scanning line signals from the second plurality of scanning line signals and generating a plurality of synthesis scanning line signals; and
performing, using the microprocessor, the frequency domain interfermetry and the adaptive signal processing by using the plurality of synthesis scanning line signals and generating a second power intensity distribution.

5. A non-transitory computer readable storage medium storing a program for causing a computer to execute the subject information obtaining method according to claim 4.

6. The subject information obtaining method according to claim 4, wherein the scanning line synthesis process includes adding the tow or more scanning line signals with a weight.

7. The subject information obtaining method according to claim 4, wherein a number of the first or second plurality of scanning line signals to be added is changed in accordance with at least one of a depth to be observed, a used frequency of the elastic wave, and a size of plurality of conversion elements.

* * * * *